(12) United States Patent
Asmussen et al.

(10) Patent No.: US 6,333,048 B1
(45) Date of Patent: Dec. 25, 2001

(54) SOLID MEDICAMENT FORM WITH ACTIVE AGENT DISTRIBUTED IN FLAT POLYMER FRAGMENTS

(75) Inventors: Bodo Asmussen, Bendorf; Walter Müller, Neuwied; Karsten Cremer, Bonn, all of (DE)

(73) Assignee: LTS Lohmann Therapie-Systeme GmbH, Neuwied (DE)

( * ) Notice: Subject to any disclaimer, the term of this patent is extended or adjusted under 35 U.S.C. 154(b) by 0 days.

(21) Appl. No.: 08/860,853

(22) PCT Filed: Jan. 10, 1996

(86) PCT No.: PCT/EP96/00073

§ 371 Date: Jul. 10, 1997

§ 102(e) Date: Jul. 10, 1997

(87) PCT Pub. No.: WO96/21428

PCT Pub. Date: Jul. 18, 1996

(30) Foreign Application Priority Data

Jan. 14, 1995 (DE) ................................. 195 00 977

(51) Int. Cl.$^7$ ................................. A61K 9/22; A61K 9/48
(52) U.S. Cl. ........................................ 424/457; 424/468
(58) Field of Search ........................... 424/484, 486–88, 424/472, 499, 501, 457, 468; 514/951–52; 428/402

(56) References Cited

U.S. PATENT DOCUMENTS

| | | | |
|---|---|---|---|
| 3,028,300 | * | 4/1962 | Cantor et al. . |
| 3,898,326 | * | 8/1975 | Cantor et al. . |
| 4,092,458 | * | 5/1978 | Hoffman . |
| 4,151,273 | | 4/1979 | Riegelman et al. .................. 424/78 |
| 4,678,684 | * | 7/1987 | Sand . |
| 4,933,360 | | 6/1990 | Pandit et al. ......................... 514/417 |
| 4,985,023 | * | 1/1991 | Blank et al. . |
| 5,622,717 | * | 4/1997 | Fuisz . |

OTHER PUBLICATIONS

Goldberg et al., *J. Pharm. Sci.*, vol. 54, pp. 1145–1148 (1965).

Sucker et al., *Pharmazeuticsch Technologie*, Thiem Verlkag 1991, pp. 249–255.

* cited by examiner

Primary Examiner—Edward J. Webman
(74) Attorney, Agent, or Firm—Wenderoth, Lind & Ponack, L.L.P.

(57) ABSTRACT

In a solid medicament form for the peroral application of active agents containing a uniform distribution of active agent in a polymer material, the polymer material is in the form of flat fragments.

12 Claims, No Drawings

SOLID MEDICAMENT FORM WITH ACTIVE AGENT DISTRIBUTED IN FLAT POLYMER FRAGMENTS

This application is a 371 application of PCT/EP96/00073, filed Jan. 10, 1996.

The invention relates to a solid drug form for peroral administration comprising one or more active compounds, which are homogeneously distributed in a polymeric material.

BACKGROUND OF THE INVENTION

Solid active compound inclusions in polymeric materials have already been known for a relatively long time and are employed in pharmaceuticals technology for pursuing various aims. One possibility of systematization of such polymer inclusions from a pharmaceutical standpoint is classification into fast-releasing drug forms and drug forms with modified or sustained release.

Polymer inclusions in fast-releasing drug forms are, as a rule, used to accelerate dissolution of the active compound in the fluids of the gastrointestinal tract. According to Noyes and Whitney, the rate of dissolution of a solid active compound is proportional to the active surface area A of the solid and the difference between the saturation concentration $C_s$ and the actual active compound concentration C according to the equation $$\frac{dC}{dt} = k_1 \cdot A \cdot (C_s - C) \cdot V^{-1} \quad (I)$$

in which V is the volume of fluid and the constant $k_1$ results from the diffusion coefficient D of the active compound in the fluid and the thickness h of the stationary diffusion layer from the formula.

One obvious pharmaceutical possibility for increasing the rate of dissolution of active compounds accordingly lies in increasing the surface area A, for example by micronization. In the case of poorly wettable active compounds, an effective increase in the surface area, according to the above equation (I), can also be achieved by addition of wetting agents, since non-wetted surfaces are not included in A.

At a very low solubility $C_s$ of the active compound, however, such measures by themselves do not always lead to the goal, since the difference ($C_s$-C) is very small and causes only a low rate of dissolution. In many of these cases, a significant improvement can be achieved by inclusion of the active compounds in polymers as solid solutions.

For example, U.S. Pat. No. 4,151,273 indicates a route for inclusion of the sparingly soluble active compound griseofulvin in polyethylene glycol as a solid solution, with which faster dissolution of the active compound in the gastrointestinal tract and therefore better bioavailability can be achieved after peroral administration than in the case of conventional formulations. Other examples of solid solutions of active compounds are to be found in J. Pharm. Sci., 54, pages 1145–1148 (1965).

Active compound inclusions in the form of solid dispersions in hydrophilic polymers can also have a positive effect on dissolution of the active compound. For example, U.S. Pat. No. 4,933,360 describes a rapidly soluble solid dispersion of chlorthalidone in polyvinylpyrrolidone which has led to significantly improved absorption of the active compound in subjects, compared with commercially available formulations.

Conversely, a significant delay in the release or in the dissolution of the active compound can be achieved by inclusion of active compounds in less readily water-soluable polymers.

These formulations can be classified into erodable and erosion-resistant matrices. Erodable matrices are to be understood as meaning those which either dissolve slowly or undergo another type of breakdown of the mass in the course of the release. In these cases, the active compound is as a rule released chiefly at the margins of the polymer. On the other hand, erosion-resistant matrices are largely retained over the course of the release; their solubility is very low and coherence high. Active compounds are released from them by diffusion, and for this reason such formulations are also called diffusion matrices.

Various processes are known for the preparation of these formulations. Mention may be made, inter alia, of so-called coprecipitates, coevaporates, coextrudates and sprayed and fused inclusions (Sucker et al., Pharmazeutische Technologie [Pharmaceutical technology], Thieme Verlag 1991, page 250 et seq.). The expert is also familiar with further processing of such inclusions by comminution to powders, mixing with further auxiliaries and subsequent tablet-making or introduction into hard gelatin capsules, if they do not lead directly to drug forms which can be administered, as in the case of some coextrudates (see, for example, U.S. Pat. No. 4,933,360). In addition, the conventional drug forms of tablet and hard gelatin capsule have the advantage that extremely efficient manufacturing technologies are available in respect of metering accuracy, production rate and profitability.

Disadvantages of the prior art are the considerable expenditure on comminution of the polymer inclusions before further processing to the final drug form. Depending on the material, the mill used and the grinding conditions, comminution of the bulk goods leads to particles of different size and different shape. From the point of view of modern requirements of the purity of medicaments, mills are usually to be rejected because of their abrasion of material. With the expensive comminution processes, there is the risk of changing the physicochemical state, for example by stress-initiated thermodynamic stabilization of originally vitreous-amorphous inclusions by crystallization or, in the case of solid suspensions, even by substantial separation of the active compound and polymer. Such serious changes can be counteracted by the choice of grinding conditions, it being necessary to avoid high stresses on the formulation, and the degree of comminution tending to be kept low. As a result, pellet-like particles of spherical to irregular shape are obtained which, nevertheless, have the disadvantage that the ratio of their spatial extent to the surface area can considerably impair release of the active compound. It can thus be explained why the rate of release of an active compound from pellet-like particles of a polymer which effects sustained release, and in which it is included, decreases constantly, after a relatively rapid initial release of the active compound located close to the surface of the particles, as a result of the continuously increasing diffusion zones in the polymer. According to the current prior art, this effect of increasing diffusion zones can be bypassed only by extremely fine grinding of the inclusion material, which is accompanied by the disadvantages and risks mentioned.

BRIEF SUMMARY OF THE INVENTION

This invention is based on the object of employing active compound inclusions in polymeric material in drug formulations in a form which does not have the disadvantages listed for the pellets and powders known in the prior art.

The object is achieved by providing a solid drug form which comprises a homogeneous distribution of active compound in polymeric material in the form of flat fragments. In this manner, it is possible to keep the diffusion zones to the polymer surface particularly short and therefore relatively constant, fine grinding being bypassed.

DETAILED DESCRIPTION OF THE INVENTION

Flat fragments in the context of this invention are pieces or sections with a plaice-, platelet- or leaf-like shape, such as are formed, for example, when film-like material is broken up. They have a considerably smaller thickness, for example 1 $\mu$m to 500 $\mu$m, compared with their length and breadth, thin films or foils being preferred.

One possibility of producing such flat particles comprises rolling out particles of spherical or irregular shape, such as can be obtained from gentle comminution processes, between two rolls rotating in opposite directions. A prerequisite for this method is a sufficient plastic deformability of the inclusion material; too high an elasticity would not lead to permanent flattening of the particles, while brittle material breaks up into smaller, irregular fragments under these conditions.

Production of flat particles from flat, film-like material is considerably more advantageous and preferred. Efficient coating techniques are available for the production of such film-like material, these also already being employed in the pharmaceuticals industry—for example for production of transdermal therapeutic systems. Brittle inclusion material can also be produced and further processed in this manner. Both solid solutions and solid dispersions can be prepared according to the invention by this method.

Alternatively, polymer films comprising homogeneously distributed active compound can also be produced by extrusion processes. Extrusion by means of a conveying apparatus and a temperature-controllable slot die and subsequent stretching is widely used in industrial film production.

It is often appropriate in the formulation of inclusion products additionally to add auxiliaries to the polymeric material, as well as the active compound. These include, for example, surfactants, plasticizers, crystallization retardants, antioxidants, acids, bases and the like.

Coarse comminution of film-like materials to flat fragments can be achieved under gentle conditions with the aid of largely abrasion-free rotary and roller crushers and with cutting machines. These machines can as a rule be adjusted such that they lead to particle sizes (length) of 0.2 to 2 mm, which is the preferred particle size for the inclusion product. The stresses on the material here are considerably lower than in the case of fine grinding or even micronization.

The drug forms which are preferred according to the invention are tablets and hard gelatin capsules, since they are easy to administer and are largely accepted by the patient, and also because the production technologies which comply with all the current requirements in respect of observing "GMP" (Good Manufacturing Practices) guidelines for producers of pharmaceuticals, in particular dosage accuracy, as well as economically efficient production of large piece numbers, are available.

In this context, the polymeric material with the included active compound and, if appropriate, auxiliaries can be mixed with further auxiliaries. These include, for example, physiologically acceptable fillers, binders, flow regulators, lubricants and release agents, antioxidants, dyestuffs or pigments, aromas, wetting agents, hydrophilizing agents, hydrophobizing agents, solubility-improving agents, disintegration modulators, substances for adjusting the pH and the like. The mixture can then be converted into tablets or introduced into hard gelatin capsules on conventional machines.

More than one active compound can also be incorporated into a drug form according to the invention, if this appears to be necessary. This can be effected in various ways. On the one hand, it is possible to include more than one active compound in the polymeric material itself. On the other hand, several inclusions can also be combined into one drug form. Finally, it is possible to have active compounds in included form in addition to non-included active compounds in the same drug form. There is thus a large number of pharmaceutical possibilities for controlling the rate of release of the individual active compounds, both together and independently of one another.

The new drug form offers an additional advantage in that it enables mucoadhesive auxiliaries to be employed therapeutically in an effective manner. In particular, if the active compound is included in a polymeric material with mucoadhesive properties or with the addition of mucoadhesive auxiliaries and the inclusion product is incorporated into a fast-disintegrating tablet or capsule, a large number of flat particles having a particularly high total contact area on the mucosa and as a result considerably improved mucoadhesiveness compared with other formulations are thus released after primary disintegration of the drug form in the gastrointestinal tract. An intensification of all the positive effects of mucoadhesion, such as, for example, prolonging the residence time in the upper sections of the gastrointestinal tract and, because of the short diffusion zone, an increased absorption rate of higher molecular weight active compounds, can be achieved here (Lenaerts et al., Bioadhesive Drug Delivery Systems, CRC Press 1990).

The release of the active compounds from the inclusions in the known polymers is considerably promoted and can easily be controlled, i.e. optionally accelerated or delayed, by the shape thereof as flat fragments. In dimensionally stable polymeric materials which remain undecomposed, the diffusion of the active compounds can also be accelerated and adjusted by choice of the film thickness. In polymeric materials which, as a result of chemical structure and molecular weight, release the active compound into the body fluid by dissolving, decomposition of the polymers, erosion or swelling, the flat form of the polymer fragments according to the invention results in greatly increased possibilities in pharmaceutical terms.

What is claimed is:

1. A peroral solid drug form in the form of a tablet or capsule having a controlled release of one or more pharmacologically active compounds by diffusion, comprising fragments having a thickness of about 1 $\mu$m to about 500 $\mu$m and comprising a polymeric material wherein the said pharmacologically active compound or compounds are homogeneously distributed, wherein the polymeric material is erosion-resistant over the course of the release of said one or more pharmacologically active compounds.

2. The solid drug form according to claim 1, in the form of fragments combined to form a tablet, wherein the fragments are pressed into the form of a tablet, directly or after mixing with one or more auxiliaries suitable for tablet making.

3. The solid drug form according to claim 1, in the form of fragments within a capsule, wherein the fragments are added to a capsule directly or after mixing with one or more pharmaceutically acceptable auxiliaries.

4. The solid drug form according to claim 1, comprising more than one active compound.

5. The solid drug form according to claim 1, wherein the one or more active compounds are present in the polymeric material as a solution.

6. The solid drug form according to claim 1, wherein the one or more active compounds are present in the polymeric material in the form of a dispersion.

7. The solid drug form according to claim 1, wherein the polymeric material further comprises auxiliaries selected from the group consisting of surfactants, plasticizers, stabilizers, crystallization retardants, antioxidants, wick substances and substances for adjusting the pH.

8. The solid drug form according to claim 1, wherein the polymeric material is in the form of a thin film.

9. The solid drug form according to claim 1, wherein the polymeric material has mucoadhesive properties.

10. The solid drug form according to claim 1, wherein when the solid drug form is placed into a release medium, the polymeric material is erodable in the release medium with or without the polymeric material retaining its chemical structure.

11. The solid drug form according to claim 1, wherein when the solid drug form is placed into a release medium, the polymeric material is swellable in the release medium.

12. The solid drug form according to claim 1, wherein the fragments are produced by a method of rolling out polymeric material particles having spherical or irregular shape and containing the pharmacologically active compound or compounds between two rolls rotating in opposite directions, or comminuting a film consisting essentially of said polymeric material and containing the said pharmacologically active compound or compounds.

* * * * *